US007323459B2

(12) United States Patent
Dolitzky et al.

(10) Patent No.: US 7,323,459 B2
(45) Date of Patent: Jan. 29, 2008

(54) CRYSTAL FORMS, METHODS FOR THEIR PREPARATION AND METHOD FOR PREPARATION OF OLANZAPINE

(75) Inventors: Ben Zion Dolitzky, Petach Tiqva (IL); Judith Aronhime, Rehovot (IL); Dov Diller, Jerusalem (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 300 days.

(21) Appl. No.: 10/746,698

(22) Filed: Dec. 24, 2003

(65) Prior Publication Data

US 2004/0198721 A1 Oct. 7, 2004

Related U.S. Application Data

(60) Provisional application No. 60/435,913, filed on Dec. 24, 2002.

(51) Int. Cl.
*A61P 25/18* (2006.01)
*A61K 31/55* (2006.01)
*C07D 495/04* (2006.01)

(52) U.S. Cl. ...................................... 514/220; 540/557

(58) Field of Classification Search ................ 514/220; 540/557

See application file for complete search history.

(56) References Cited

U.S. PATENT DOCUMENTS 5,229,382 A 7/1993 Chakrabarti et al. ........ 514/220
5,631,250 A * 5/1997 Bunnell et al. ............. 514/220
5,637,584 A 6/1997 Larsen ....................... 514/220
5,703,232 A 12/1997 Bunnell et al. ............. 540/557
5,736,541 A 4/1998 Bunnell et al. ............. 514/220
6,008,216 A 12/1999 Chakrabarti et al. ........ 514/220
6,020,487 A 2/2000 Bunnell et al. ............. 540/557
6,169,084 B1 1/2001 Bunnell et al. ............. 514/220
6,251,895 B1 6/2001 Larsen et al. ............... 514/220
6,348,458 B1 2/2002 Hamied et al. ............. 514/220
6,740,753 B2 5/2004 Davies et al. ............... 540/557
6,906,062 B2 6/2005 Chhabada et al. .......... 514/220
7,022,698 B2 4/2006 Hamied et al. ............. 514/220
2004/0048854 A1 3/2004 Patel et al. ................. 514/220
2004/0067936 A1 4/2004 Reguri et al. ............... 514/220
2005/0153954 A1 7/2005 Reguri et al. ............... 514/220
2005/0239772 A1 10/2005 Piechaczek et al. ........ 514/220
2005/0267099 A1 12/2005 Keltjens et al. ............. 514/220
2005/0272720 A1 12/2005 Keltjens ...................... 514/220
2005/0272721 A1 12/2005 Keltjens ...................... 514/220
2006/0040920 A1 2/2006 Kotar Jordon et al. ..... 514/220

FOREIGN PATENT DOCUMENTS

EP 0 733 634 9/1996
EP 0 733 635 8/2001
EP 0 831 098 11/2001
WO WO 02/18390 3/2002
WO WO 02/060906 8/2002
WO WO 03/037903 5/2003
WO WO 03/091260 11/2003
WO WO 03/097650 11/2003
WO WO 2004/000847 12/2003
WO WO 2004/056833 7/2004
WO WO 2004/065390 8/2004
WO WO 2004/113346 12/2004
WO WO 2005/080401 9/2005
WO WO 2005/085256 9/2005
WO WO 2005/090359 9/2005
WO WO 2005/107375 11/2005
WO WO 2006/006180 1/2006
WO WO 2006/006185 1/2006
WO WO 2006/010620 2/2006
WO WO 2006/013435 2/2006
WO WO 2006/025065 3/2006
WO WO 2006/027800 3/2006
WO WO 2006/030300 3/2006

OTHER PUBLICATIONS

Polla, G.I, et al., "Thermal behaviour and stability in Olanzapine", International Journal of Pharmaceutics, v. 301 (2005) pp. 33-40.
Reutzel-Edens et al., *Anhydrates and Hydrates of Olanzapine: Crystallization, Solid-State Characterization, and Structural Relationship*, "Crystal Growth and Design", 2003, 3, 897-907.

* cited by examiner

*Primary Examiner*—Brenda Coleman
(74) *Attorney, Agent, or Firm*—Kenyon & Kenyon LLP

(57) ABSTRACT

The invention is directed to a series of novel crystalline olanzapine forms, in particular hydrated and solvated crystalline forms of olanzapine, methods of use in pharmaceutical compositions, and method of treating psychiatric disorders using the crystalline forms. One series of the crystalline forms are hydrates, i.e. water containing crystals, wherein water may be present in a ratio of about 2:1.5 to a ratio of about 1:3 olanzapine:water, while another includes solvates such as an isobutanol solvate. The olanzapine crystalline forms include Forms H, G, Y, X, K, S, Q, Z, and J.

18 Claims, 9 Drawing Sheets

CRYSTAL FORMS, METHODS FOR THEIR PREPARATION AND METHOD FOR PREPARATION OF OLANZAPINE

CROSS-REFERENCE TO RELATED APPLICATION

This application claims the benefit under 35 U.S.C. § 1.119(e) of Provisional Application Ser. No. 60/435,913 filed Dec. 24, 2002, the disclosure of which is incorporated by reference in its entirety herein.

FIELD OF THE INVENTION

The present invention is directed to crystal structures of olanzapine, methods of preparing the crystal structures, and use of the crystal structures. In particular, the invention is directed to polymorphic forms of olanzapine, pharmaceutical formulations thereof, and methods of treating psychiatric disorders.

BACKGROUND OF THE INVENTION

Olanzapine is an antagonist of dopamine at D-1 and D-2 receptors and has antimuscarinic anti-cholinergic properties and antagonist activity at 5HT-2 receptor sites. Olanzapine also has antagonist activity at noradrenergic alpha-receptors. The above-identified properties indicate that olanzapine is a potential neuroleptic with relaxant, anxiolytic, or anti-emetic properties, and is useful in treating psychotic conditions such as schizophrenia, schizophreni-form diseases, and acute mania. At lower doses olanzapine can be used in the treatment of mild anxiety states. Olanzapine has also been reported as having a high level of activity in the clinical evaluation of psychiatric patients suffering from schizophrenia and it exhibits this high activity at surprisingly low dosage levels.

Olanzapine has shown great promise in the treatment of psychotic patients. Unfortunately, olanzapine typically exhibits a color which is undesirable for commercial pharmaceutical use, especially since the color was found to change over time on exposure to air. Carbon treatment of olanzapine did not removed the undesired color. A pharmaceutical that changes color over time could be particularly troublesome for psychotic patients if a dosage form, such as a tablet, was chosen where color changes were apparent. Consequently, there have been many attempts to provide novel olanzapine polymorphs.

Polymorphic forms and hydrate/solvate forms of olanzapine have been disclosed in various patents and publications. For example, U.S. Pat. No. 5,736,541 ("the '541 patent") and EP Patent No. 733 635 disclose olanzapine Form II, an anhydrate, however, as disclosed Form II may be difficult to prepare in the absence of technical grade olanzapine or alternative methods for preparing olanzapine. The '541 patent discloses that the prior known Form I of olanzapine, as prepared by the procedures described in U.S. Pat. No. 5,229,382, is metastable and unsuitable for commercial use due to discoloration of the compound over time. U.S. Pat. No. 5,637,584 discloses a monosolvate of dichloromethane identified as Form I, however as discussed above, Form I may be unsuitable for commercial use. U.S. Pat. No. 5,703,232 and EP Patent No. 733,634 disclose olanzapine, which while free of water and acetonitrile, contains solvates of methanol, ethanol, and isopropanol. U.S. Pat. No. 6,020,487 and EP Patent No. 831,098 disclose dihydrate forms of olanzapine, selected from dihydrate B, dihydrate D, and dihydrate E, which may be used for the preparation of anhydrate olanzapine. Each of the above-identified patents identifies a different crystalline form of olanzapine as identified by X-ray diffraction peaks and their relative intensities.

U.S. Pat. No. 6,348,458 discloses Form III, Form IV, and Form V olanzapine, which are anhydrates produced under aqueous conditions. Form III, Form IV, and Form V olanzapine are synthesized by dissolving olanzapine in mineral acid, followed by reaction with base, and precipitation of the crystalline form. PCT publication WO 02/18390 discloses olanzapine as monohydrate-I and dihydrate-I and WO 02/060906 discloses olanzapine as Form X. In addition to X-ray powder diffractions, FTIR or DSC were used to identify the crystalline olanzapine.

Despite the many attempts by the prior art, there is a need to obtain desirable olanzapine crystals with fewer purification steps, that lacks the harshness of mineral acids, or additional synthetic steps. The present invention provides novel crystalline forms of olanzapine that avoid the synthetic and purification pitfalls of the prior art.

SUMMARY OF THE INVENTION

One embodiment of the invention encompasses crystalline olanzapine isobutanol solvate. Another embodiment encompasses a crystalline form of olanzapine characterized by a powder X-ray diffraction pattern having peaks at about 8.7, 18.4, 19.2, 20.0, 21.1, 21.6, 22.4, 23.1, 23.6 and 24.0, ±0.2 degrees two-theta, which may have additional peaks at about 10.4, 12.5, 14.1, 14.7, 17.2, 17.9, 24.9 and 25.4±0.2 degrees two-theta. The crystalline form may be an isobutanol solvate. Yet another embodiment of the invention encompasses a crystalline form of olanzapine having a powder X-ray diffraction pattern substantially as depicted in FIG. 1. A process for preparing the crystalline form of olanzapine may comprise the steps of dissolving olanzapine in isobutanol, cooling the mixture, and isolating the crystals.

Another embodiment of the invention encompasses a crystalline form of olanzapine characterized by a powder X-ray diffraction pattern having peaks at about 6.6, 9.0, 16.4, 17.9, 18.6, 18.8, 19.6, 22.8 and 25.2, ±0.2 degrees two-theta, which may have additional peaks at about 14.3, 14.8, 20.5, 23.2, 23.8, 24.2±0.2 degrees two-theta. The crystalline form may be a dihydrate. Yet another embodiment encompasses a crystalline form of olanzapine having a powder X-ray diffraction pattern substantially as depicted in FIG. 2. A process for preparing the crystalline form of olanzapine comprises the steps of creating a slurry of olanzapine dihydrate in methyl tertiary-butyl ether, stirring the mixture, and isolating the crystals.

Another embodiment of the invention encompasses a crystalline form of olanzapine characterized by a powder X-ray diffraction pattern having peaks at about 8.4, 8.8, 9.3, 16.9, 18.4, 19.4, 20.1, 22.2, 23.1, 23.8 and 25.2, ±0.2 degrees two-theta, which may have additional peaks at about 14.2, 14.5 and 18.9±0.2 degrees two-theta. The crystalline form may be a hydrate. Yet another embodiment of the invention encompasses a crystalline form of olanzapine having a powder X-ray diffraction pattern substantially as depicted in FIG. 3. A process for preparing the crystalline form comprises the steps of dissolving olanzapine in methylene chloride to form a solution; adding cyclohexane to the solution; cooling the solution; and isolating the crystals. Optionally, the solution is formed by heating.

Another embodiment of the invention encompasses a crystalline olanzapine sesquihydrate. One embodiment of the invention encompasses a crystalline form of olanzapine characterized by a powder X-ray diffraction pattern having peaks at about 9.1, 16.4, 18.5, 22.8, 23.8 and 24.3±0.2 degrees two-theta, which may have additional peaks in the powder X-ray diffraction pattern at about 9.1, 16.4, 18.5, 22.8, 23.8 and 24.3±0.2 degrees two-theta. The crystalline form may be a sesquihydrate. Yet another embodiment of the invention encompasses a crystalline form of olanzapine having a powder X-ray diffraction pattern substantially as depicted in FIG. 4. A process for preparing the crystalline form comprises the steps of dissolving olanzapine in an aqueous solution of HCl; precipitating the crystalline form by adding base; and isolating the crystals. Optionally, the olanzapine is dissolved by heating or the pH prior to isolating the crystals is about 8.5. The process may further comprise cooling the solution prior to isolating the crystals.

Another embodiment of the invention encompasses a crystalline olanzapine trihydrate. One embodiment of the invention encompasses a crystalline form of olanzapine characterized by a powder X-ray diffraction pattern having peaks at about 8.8, 13.7, 16.3, 18.4, 19.6, 20.2 and 22.4±0.2 degrees two-theta, which may have additional peaks in the powder X-ray diffraction pattern at about 15.1, 15.3, 23.0, 24.0, 24.4, 25.1 and 29.7±0.2 degrees two-theta. The crystalline form may be a trihydrate. Yet another embodiment of the invention encompasses a crystalline form of olanzapine having a powder X-ray diffraction pattern substantially as depicted in FIG. 5. A process for preparing the crystalline form comprises the steps of dissolving olanzapine in a solution of acetic acid and water; filtering the solution; stirring the solution; precipitating the crystalline form by adding a base; and isolating the crystals. Optionally, the solution is stirred at about 20° C.; the base is ammonium hydroxide; or the pH prior to step isolating the crystals is about 9.8.

Another embodiment of the invention encompasses a crystalline form of olanzapine characterized by a powder X-ray diffraction pattern having peaks at about 8.6, 10.3, 11.4, 14.6, 19.8, 21.0, 21.5, 22.3, 23.9 and 29.7, ±0.2 degrees two-theta, which may have additional peaks in the powder X-ray diffraction pattern at about 12.5, 17.0, 17.8, 19.0 and 25.2±0.2 degrees two-theta. The crystalline form may be a dihydrate. Yet another embodiment of the invention encompasses a crystalline form of olanzapine having a powder X-ray diffraction pattern substantially as depicted in FIG. 9. A process for preparing the crystalline form comprises the steps of heating Form X olanzapine at a temperature of at least about 100° C. Optionally, the heating temperature is about 160° C.

Another embodiment of the invention encompasses a crystalline olanzapine ¾ hydrate. Yet another embodiment of the invention encompasses a crystalline form of olanzapine characterized by a powder X-ray diffraction pattern having peaks at about 8.7, 14.7, 17.1, 17.8, 19.9, 21.0, 21.6, 22.3, 23.9, 25.3 and 26.5±0.2 degrees two-theta, which may have additional peaks in the powder X-ray diffraction pattern at about 9.2, 9.4, 10.4, 11.5, 11.9, 12.5 and 29.7±0.2 degrees two-theta. The crystalline form of olanzapine may be a ¾ hydrate. Another embodiment of the invention encompasses a crystalline form of olanzapine having a powder X-ray diffraction pattern substantially as depicted in FIG. 8. A process for preparing the crystalline form comprises the steps of heating Form J at a temperatures of at least about 100° C. Optionally, the heating temperature is about 130° C. Another process for preparing the crystalline form comprises exposing Form II at 100% relative humidity for a period of time ranging between 2 weeks and 2 months. Optionally, the period of time is about 1 month.

Another embodiment of the invention encompasses a crystalline form of olanzapine characterized by a powder X-ray diffraction pattern having peaks at about 8.8, 18.1, 18.8, 19.3, 22.9, 23.3 and 24.8±0.2 degrees two-theta, which may have additional peaks in the powder X-ray diffraction pattern at about 8.2, 12.8, 13.8, 14.3, 14.9, 24.3 and 25.7±0.2 degrees two-theta. The crystalline form of olanzapine may be a dihydrate. Yet another embodiment of the invention encompasses a crystalline form of olanzapine having a powder X-ray diffraction pattern substantially as depicted in FIG. 6. A process for preparing the crystalline form comprises the steps of dissolving olanzapine in an organic solvent; adding water; cooling the solution; and isolating the crystals. The organic solvent may be selected from the group consisting of DMSO, dioxane and acetone. The organic solvent may be heated to about 80° C.

Another embodiment of the invention encompasses a crystalline form of olanzapine characterized by a powder X-ray diffraction pattern having peaks at about 9.0, 16.3, 18.5, 19.6, 20.0, 20.4, 22.8, 24.2, and 25.6±0.2 degrees two-theta, which may have additional peaks in the powder X-ray diffraction pattern at about 17.1, 17.5, 21.2, 23.4, 23.7 and 27.6±0.2 degrees two-theta. The crystalline olanzapine may be a dihydrate. Yet another embodiment of the invention encompasses a crystalline form of olanzapine having a powder X-ray diffraction pattern substantially as depicted in FIG. 7. A process for preparing the crystalline form comprises the steps of dissolving olanzapine in a mixture of ethyl acetate and toluene; heating the mixture; cooling the mixture; adding water to the mixture; cooling the mixture; and isolating the crystals. Optionally, the mixture is heated to about 80° C.; the mixture is cooled during the first time to about 60° C.; the mixture is cooled during the second time to room temperature. A process for preparing olanzapine crystalline Form II comprising drying the Form Z, Form H, or Form Q crystalline olanzapine.

One embodiment of the invention encompasses a process for preparing olanzapine crystalline Form V comprising drying the Form G crystalline olanzapine.

Yet another embodiment of the invention encompasses a pharmaceutical composition comprising the crystalline forms of olanzapine selected from the group consisting of Forms H, G, Y, X, K, S, Q and J.

BRIEF DESCRIPTION OF THE DRAWINGS

The invention will be further described with reference to the following non-limiting figures.

DETAILED DESCRIPTION OF THE INVENTION

Figure 1:
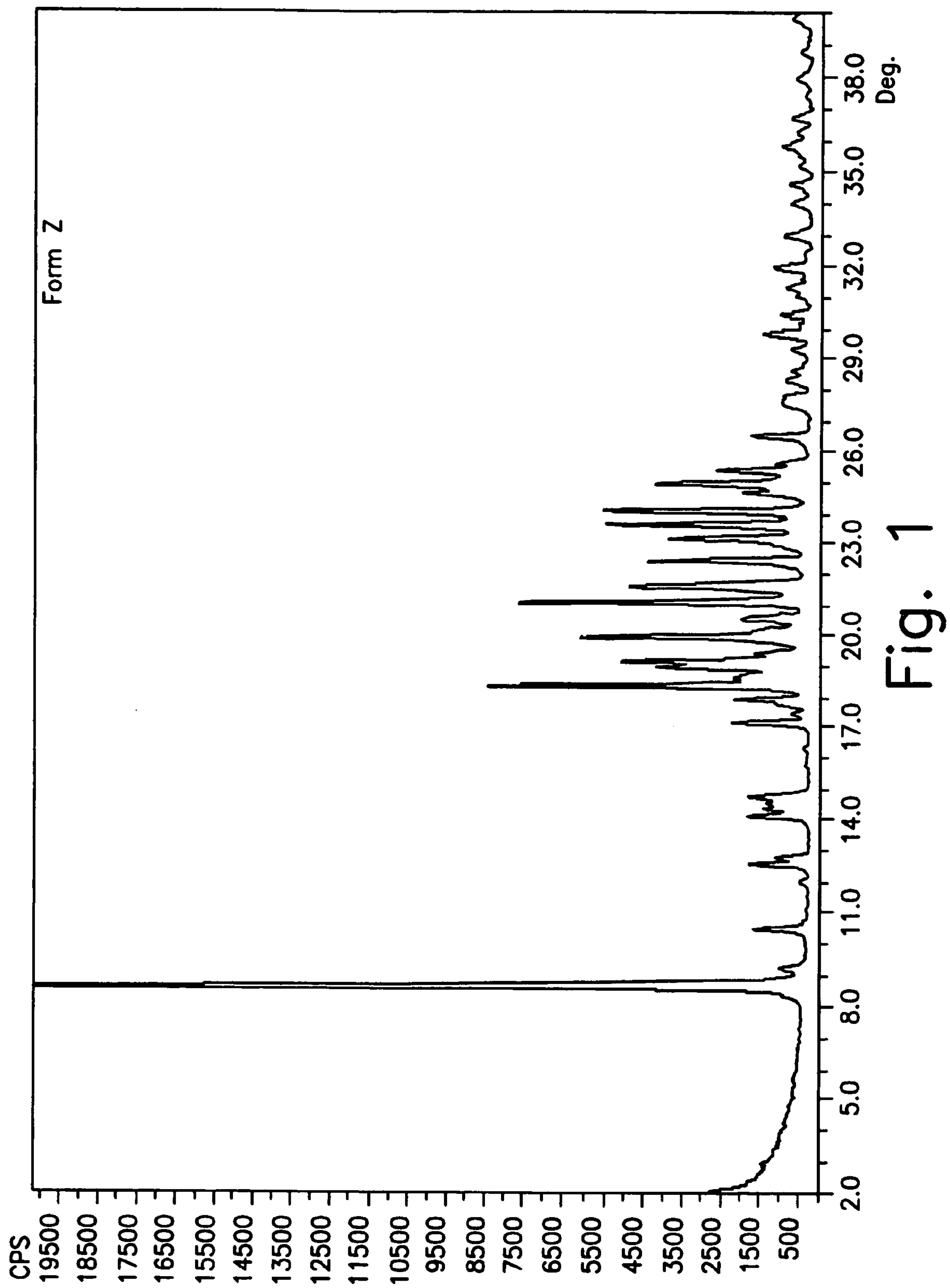
FIG. 1 illustrates the X-ray powder diffraction pattern of olanzapine Form Z.
Figure 2:
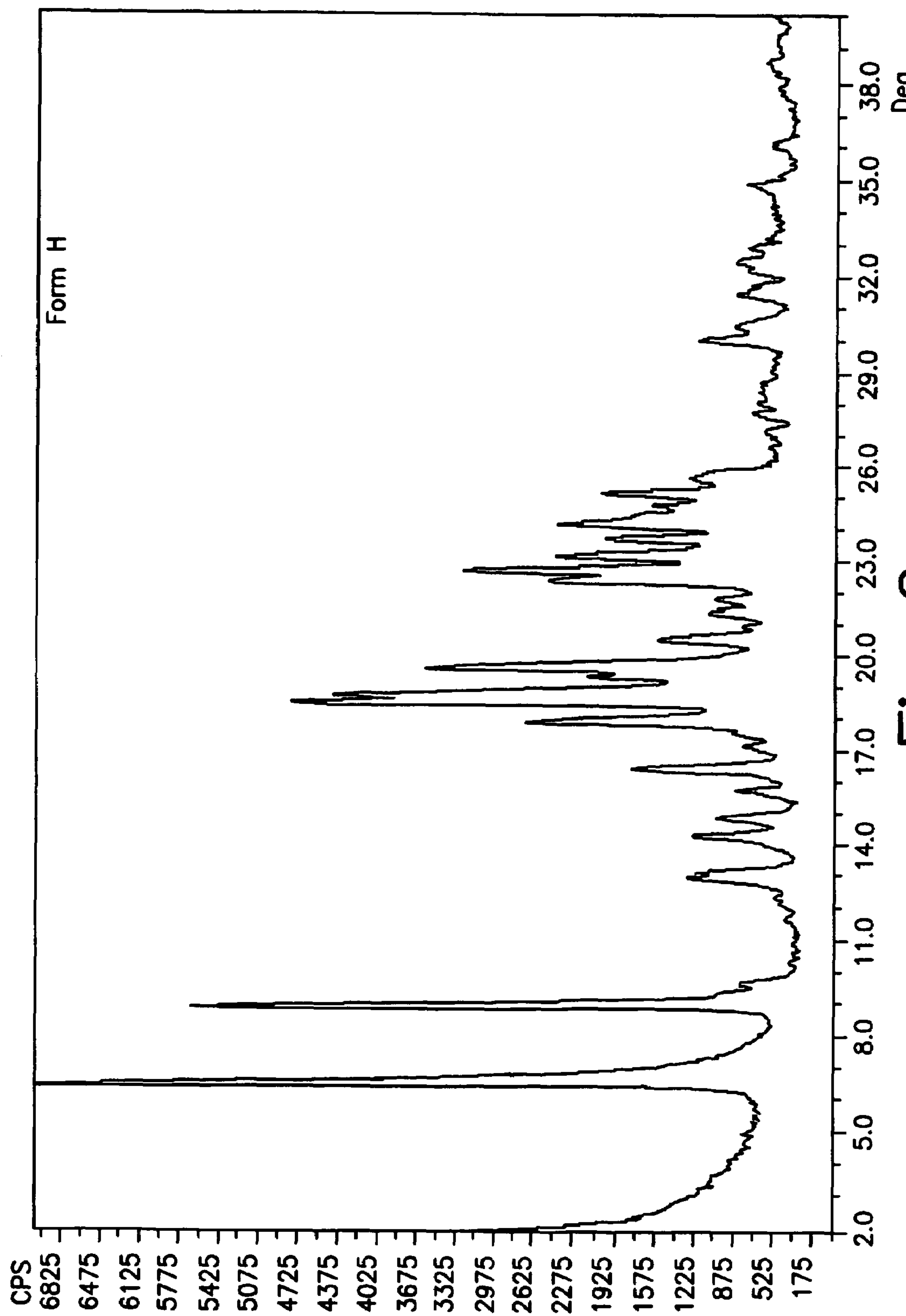
FIG. 2 illustrates the X-ray powder diffraction pattern of olanzapine Form H.
Figure 3:
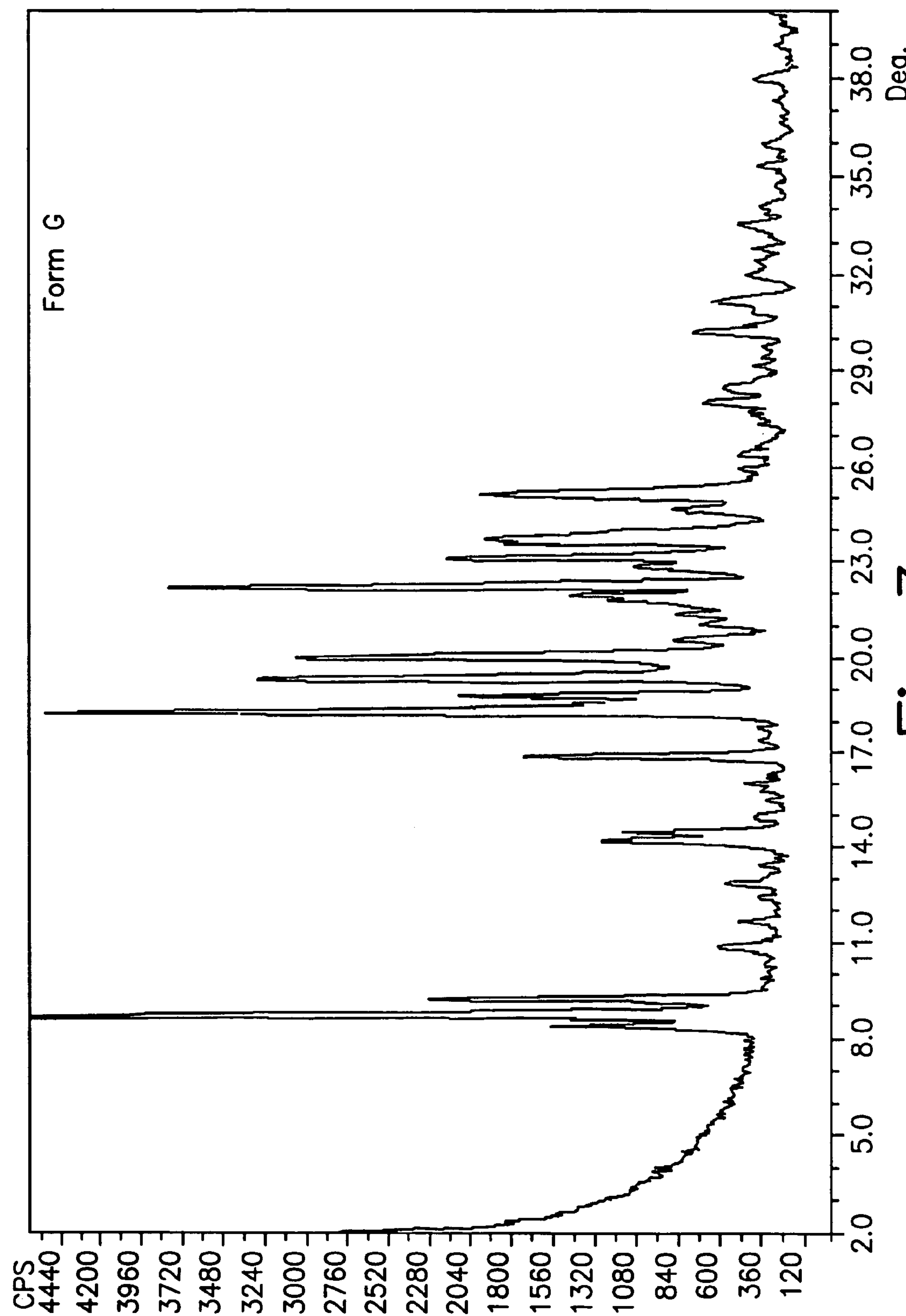
FIG. 3 illustrates the X-ray powder diffraction pattern of olanzapine Form G.

The present invention encompasses a series of novel crystalline olanzapine forms, in particular solvated crystalline forms, methods of use in pharmaceutical compositions, and method of treating psychiatric disorders using the crystalline forms. In particular, one series of the crystalline forms are hydrates, i.e. water containing crystals, wherein water may be present in a ratio of about 2:1.5 to a ratio of about 1:3 olanzapine:water. Another crystalline form is a crystalline olanzapine isobutanol solvate.

One embodiment of the invention encompasses a crystalline form of olanzapine, herein denominated as Form Z. Form Z is an isobutanol solvate form, in particular a hemisolvate of isobutanol. Form Z is characterized in part by X-ray peaks at about 8.7, 10.4, 12.5, 14.1, 14.7, 17.2, 17.9, 18.4, 19.2, 17.2, 17.9, 18.4, 19.2, 20.0, 21.1, 21.6, 22.4, 23.1, 23.6, 24.0, 24.9, and 25.4 degrees two-theta. The data reported herein is within experimental error, such as within ±0.2 degrees two-theta. The main characterizing peaks are at 8.7, 18.4, 19.2, 20.0, 21.1, 21.6, 22.4, 23.1, 23.6, 24.0 degrees two-theta. Form Z is prepared by crystallizing olanzapine in isobutanol, one of ordinary skill in the art with little or no experimentation can easily determine the necessary crystallization parameters. Typically, the crystallization process comprises dissolving olanzapine in isobutanol at about 80° C., cooling the dissolved olanzapine—isobutanol solution in an ice bath, and collecting the crystals. If necessary, as understood by the skilled artisan, the crystallization process may include seeding, chilling, scratching the glass of the reaction vessel, and other such common crystallization techniques. If Form Z is dried, such as under vacuum, then the crystalline structure is converted into Form II.

Another embodiment of the invention, encompasses a crystalline olanzapine form herein denominated as Form H. Form H is a crystalline dihydrate of olanzapine. Form H is characterized in party by X-ray peaks at about 6.6, 9.0, 14.3, 14.8, 16.4, 17.9, 18.6, 18.8, 19.6, 20.5, 22.8, 23.2, 23.8, 24.2, 25.2 degrees two-theta. The main peaks are at 6.6, 9.0, 16.4, 17.9, 18.6, 18.8, 19.6, 22.8, 25.2 degrees two-theta. Form H is formed by creating a slurry of olanzapine dihydrate in methyl tertiary-butyl ether ("MTBE"), stirring the mixture, and collecting the crystals. If Form H is dried, then the crystalline structure is converted to Form II.

One embodiment of the invention, encompasses a crystalline olanzapine form herein denominated Form G. Form G is a hydrate form of olanzapine. If Form G is dried, then the crystalline structure is converted into Form V. Form G is characterized in part by X-ray peaks at 8.4, 8.8, 9.3, 14.2, 14.5, 16.9, 18.4, 18.9, 19.4, 20.1, 22.2, 23.1, 23.8, 25.2 degrees two-theta. The main peaks are at 8.4, 8.8, 9.3, 16.9, 18.4, 19.4, 20.1, 22.2, 23.1, 23.8, 25.2 degrees two-theta. Form G is obtained by dissolving olanzapine in methylene chloride while heating, adding cyclohexane, cooling the solution in an ice bath, and collecting the crystalline olanzapine.

Another embodiment of the invention encompasses a crystalline olanzapine sesquihydrate.

Another embodiment of the invention, encompasses a crystalline olanzapine form herein denominated Form Y. Form Y contains water in about 8.5% by weight, as a sesquihydrate. Form Y is characterized in part by X-ray peaks at 9.1, 16.4, 17.2, 17.5, 18.5, 19.7, 20.6, 21.3, 22.8, 23.8, 24.3, 25.6, 27.7 degrees two-theta. The main peaks are at 9.1, 16.4, 18.5, 22.8, 23.8, 24.3 degrees two-theta. Form Y is obtained by dissolving olanzapine in an aqueous solution of HCl (1.6%) while heating the solution, while hot precipitating the crystalline form by adding 10% NaOH to obtain a pH of about 8.5, cooling the solution in an ice bath, and collecting the crystals. Before drying, in the wet form, Form Y may contain up to 43% water. Bases include, but are not limited to, NaOH, $NaHCO_3$, $Na_2CO_3$, KOH, $KHCO_3$, $K_2CO_3$.

One embodiment of the invention encompasses a crystalline olanzapine trihydrate.

Another embodiment of the invention encompasses a crystalline olanzapine form herein denominated as Form X. Form X contains water in about 13-15% by weight, and is a trihydrate. Form X is characterized in part by X-ray peaks at 8.8, 13.7, 15.1, 15.3, 16.3, 18.4, 19.6, 20.2, 22.4, 23.0, 24.0, 24.4, 25.1, 29.7 degrees two-theta. The main peaks are at 8.8, 13.7, 16.3, 18.4, 19.6, 20.2, 22.4 degrees two-theta. Form X is prepared by dissolving olanzapine in a solution of acetic acid and water, filtering the solution, and stirring at about 20° C., precipitating the crystal by adjusting the pH to about 9.8 with an ammonium solution, and collecting the crystals by filtration. Preferably, the acetic acid:water ratio is about 1:1.3.

Another embodiment of the invention encompasses a crystalline olanzapine form herein denominated Form K. Form K contains water in about up to 12% by weight, and is a dihydrate. Form K is characterized in part by X-ray peaks at 8.6, 10.3, 11.4, 12.5, 14.6, 17.0, 17.8, 19.0, 19.8, 21.0, 21.5, 22.3, 23.9, 25.2, 29.7 degrees two-theta. The main peaks are at 8.6, 10.3, 11.4, 14.6, 19.8, 21.0, 21.5, 22.3, 23.9, 29.7 degrees two-theta. Form K is obtained by heating olanzapine Form X at temperatures above 100° C. for a time dependent upon on the temperature and quantity employed. For small samples and elevated temperatures, such as 50 mg to 100 mg and a temperature of 160° C., a period of 15 minutes is sufficient. For larger quantities or lower temperatures the duration of time has to be adequate in order to bring the transformation to completion, which may be monitored using X-ray diffraction.

One embodiment of the invention encompasses a crystalline olanzapine ¾ hydrate.

Another embodiment of the invention encompasses a crystalline olanzapine form herein denominated Form S. Form S contains water in about 4% by weight, as a ¾ hydrate. Form S is characterized in part by X-ray peaks at 8.7, 9.2, 9.4, 10.4, 11.5, 11.9, 12.5, 14.7, 17.1, 17.8, 19.9, 21.0, 21.6, 22.3, 23.9, 25.3, 26.5, 29.7 degrees two-theta. The main peaks are at 8.7, 14.7, 17.1, 17.8, 19.9, 21.0, 21.6, 22.3, 23.9, 25.3, 26.5, degrees two-theta. Form S is obtained by heating olanzapine Form J at temperatures above 100° C. for a period of time dependent on the temperature and quantity used. For small samples and elevated temperatures, such as 50-100 mg and a temperature of 160° C., a period of 15 minutes is sufficient. For larger quantities or lower temperatures the time duration may be adjusted to complete the transformation. Also Form S may be obtained by exposing Form II at elevated relative humidity, preferably 100% RH, for a period of time ranging from about 2 weeks to about 2 months, preferably, for about 1 month.

Another embodiment of the invention encompasses a crystalline olanzapine form herein nominated Form Q. Form Q contains water up to 12% by weight and is a dihydrate form. Form Q is characterized in part by X-ray peaks at 8.2, 8.8, 12.8, 13.8, 14.3, 14.9, 18.1, 18.8, 19.3, 22.9, 23.3, 24.3, 24.8, 25.7 degrees two-theta. The main peaks are at 8.8, 18.1, 18.8, 19.3, 22.9, 23.3, 24.8 degrees two-theta. Form Q is obtained by crystallizing olanzapine in mixtures of water with an organic solvent. Examples of organic solvents include, but are not limited to, DMSO, dioxane, or acetone. Typically, Form Q is obtained by heating an organic solvent to about 80° C.; dissolving olanzapine in the heated organic solvent; adding water; cooling the solution in an ice bath, and collecting the crystals by filtration. Form Q may be converted into Form II by drying.

One embodiment of the invention encompasses a crystalline olanzapine form herein of denominated as Form J. Form J is a dihydrate crystalline form. Form J is characterized in part by X-ray peaks at 9.0, 16.3, 17.1, 17.5, 18.5, 19.6, 20.0, 20.4, 21.2, 22.8, 23.4, 23.7, 24.2, 25.6, 27.6 degrees two-theta. The main peaks are at 9.0, 16.3, 18.5, 19.6, 20.0, 20.4, 22.8, 24.2, 25.6 degrees two-theta. Form J is obtained by dissolving olanzapine in a mixture of ethylacetate/toluene in a ratio of about 16:1 heated to about 80° C., cooling the mixture to about 60° C., adding water dropwise, cooling the solution to room temperature, and collecting the crystals by filtration. Drying Form J converts the crystalline olanzapine into Form S.

Table 1 summarizes some of the embodiment of the invention.

TABLE 1

Summary

| Experiment | Solvent | Form (wet) | Water content (%) | LOD (%) | Form (dry) |
|---|---|---|---|---|---|
| 1 | isobutanol | Z | 3.6 | 9.5 | II |
| 2 | Acetone/water | Q | 9.0 | 12.4 | II |
| 3 | Dioxane/water | Q | 5.7 | 8.9 | II |
| 4 | DMSO/water | Q | 11.7 | 10.7+ 7.4+ | II |
| 5 | Methylenechloride/ hexane | G | 7.0 | 12.1 | V |
| 6 | MTBE | H | 10.3 | 16.8 | II |
| 7 | Acetic acid/water + ammonia | X | 11.3 | 13-15 | K (heat at high temperatures) |
| 8 | HCl/water + ammonia | Y | 8.5 | 8.5 | Y |
| 9 | Ethylacetate/toluene + water | J | 10.7 | 10.6 | S (heat at high temperatures) |
| | Exposing Form II at 100% RH 1 month | S | 4.2 | | |
| | Heating form X | K | 13% | | |

Olanzapine has been found to have a wide range of therapeutic effects, particularly for the treatment of schizophrenia, schizophreniform disorders, psychosis, mild anxiety states and functional bowel disorders.

Pharmaceutical formulations according to the invention comprise substantially pure Form G, H, J, K, Q, S, X, or Y olanzapine or a pharmaceutically acceptable salt thereof as an active ingredient together with one or more pharmaceutically acceptable carriers, excipients or diluents. Any conventional technique may be used for the preparation of pharmaceutical formulations according to the invention. Examples of suitable carriers include, but are not limited to, sugars, starches, gum acacia, calcium phosphate, alginates, tragacanth, gelatin, syrup, methyl cellulose, methyl- and propyl-hydroxy-benzoate, talc, magnesium stearate or mineral oil. The active ingredient may be contained in a formulation that provides quick release, sustained release, or delayed release after administration to the patient.

As used herein "substantially pure" refers to an olanzapine crystal form associated with less than about 5% of another crystal form, preferably less than about 2%, and more preferably less than about 1% of another crystal form by weight of the total olanzapine.

Pharmaceutical compositions may be formulated for transdermal delivery, oral delivery or as a suppository. Formulations may be in the form of capsules, tablets or gels for oral delivery or as a suspension for transdermal delivery. Pharmaceutical compositions according to the present invention may contain about 0.25 mg to about 100 mg of active ingredient or, preferably, about 1 mg to about 30 mg active ingredient, along with a pharmaceutically acceptable carrier.

Having described the invention with reference to certain preferred embodiments, other embodiments will become apparent to one skilled in the art from consideration of the specification. The invention is further defined by reference to the following examples describing in detail the compositions, preparation of the compositions, and methods of administration of the invention. It will be apparent to those skilled in the art that many modifications, both to materials and methods, may be practiced without departing from the scope of the invention.

EXAMPLES

Water content was measured using the Karl Fisher technique (USP method). Weight loss was measured using TGA analysis (Mettler Toledo TG50). TGA analysis was performed with a Mettler TG50, the sample size was about 10 mg and the samples were scanned at a rate of 10° C./min from 25° C. to 200° C. The oven was constantly purged with nitrogen gas at a flow rate of 40 ml/min. Standard alumina crucibles covered by lids with one hole were used. X-ray powder diffraction data were obtained using methods known in the art and by using a SCINTAG powder X-ray diffractometer model XTRA equipped with a solid state detector. Copper radiation of 1.5418 Å was used. A round aluminum sample holder with round zero background quartz plate, with cavity of 25(diameter)*0.5(depth) mm.

Experiment 1

Preparation of Form Z

Four grams of olanzapine (4 g) were dissolved in 45 ml of isobutanol using a 80° C. water bath. Thereafter, the solution was stirred over night at room temperature and cooled in an ice bath for 1 h. The resulting crystals were collected by filtration and determined to be of Form Z. The Form Z crystals were dried for 2.5 h in a vacuum oven at 65° C. Upon analysis, the dry crystals were identified as polymorph II. Yield 2.45 g.

Experiment 2

Preparation of Form Q

Four grams of olanzapine (4 g) were dissolved in 90 ml of acetone using an 80° C. water bath. Upon addition of 65 ml of water, crystals precipitated from solution. The material was stirred overnight. The solution and crystals were cooled in ice and the crystals were collected by filtration in a yield of 87.5%.

Experiment 3

Preparation of Form Q

Four grams of olanzapine (4 g) were dissolved in 24 ml dioxane and heated in an 80° C. water bath. Upon additional of water (8 ml), crystals precipitated from the solution. The solution was reheated in the water bath and left overnight at room temperature with stirring. Subsequently, the solution was cooled in an ice bath and the crystals collected by filtration in a yield of 93.5%.

Experiment 4

Preparation of Form Q

Four grams of olanzapine (4 g) were dissolved in 8 ml DMSO by heating in a water bath at 80° C. Upon addition of water (1 ml), crystals precipitated from solution. The solution was left to stir at room temperature for 48 hours, and subsequently cooled in ice bath. The crystals were collected by filtration in a yield of 100%.

Experiment 5

Preparation of Form G

Olanzapine (4 g) was dissolved in 50 ml methylene chloride while heating. Cyclohexane (100 ml) was added with stirring. Thereafter, the solution was cooled in an ice bath and crystals were collected by filtration in a yield of 53.3%.

Experiment 6

Preparation of Form H

Olanzapine dihydrate (2 g) was slurried in MTBE (10 ml). The slurry was stirred overnight. Thereafter, the crystals were collected by filtration in a yield of 98%.

Experiment 7

Preparation of Form X

Olanzapine (10 g) was dissolved in a solution of acetic acid (30 ml) and water (40 ml). The solution was filtered through Celite and GF/F paper and stirred at 20° C. Thirty (30) ml of 25% ammonium hydroxide were added and the pH of the solution was approximately 5.9. The solution was stirred for 30 min, upon which the solution became cloudy, but nothing precipitated. Thereafter, an additional 34 ml of ammonia solution was added and the pH was 9.75. A crystal precipitated and was collected by filtration in a yield of 68.5%.

Experiment 8

Preparation of Form Y

Olanzapine (10 g) was dissolved in 110 ml HCl 1.6% while heating. The hot solution was filtered through GF/F filter paper. While still hot, the pH was adjusted to 8.5 by slowly adding 10% NaOH with stirring. During base addition, crystals formed. The solution was stirred for 30 min in an ice bath and the crystals were collected by filtration in a yield of 100%.

Experiment 9

Preparation of Form J

Olanzapine (6 g) was slurried in 120 ml ethyl acetate and 7.2 ml toluene. The mixture was heated to 80° C. and the materials dissolved. Thereafter, the mixture was cooled to 60° C. and water (12 ml) was added with stirring by dripping in with a Pasteur pipette. The solution was allowed to cool to room temperature with stirring and crystalls appeared. The solution was stirred for approximately 1½ hours at room temperature. Thereafter, the crystals were collected by filtration in a yield of 63.3%.

Experiment 10

Preparation of Form S

Form J, made as described above, was kept in an oven at 130° C. for 40 minutes. Thereafter, the crytals were collected to obtain Form S crystalline olanzapine.

Experiment 11

Preparation of Form S

A small aliquot of Form II (about 50 mg) was exposed to 100% relative humidity for a period of 1 month. Thereafter, the crytals were collected to obtain Form S crystalline olanzapine.

Experiment 12

Preparation of Form K

Form X, made as described above, was kept at 130° C. for about 40 minutes. Form X was kept at 160° C. for about 15 minutes. Thereafter, the crystals were collected to obtain Form K crystalline olanzapine.

What is claimed is:

1. Crystalline olanzapine sesquihydrate.

2. A crystalline form of olanzapine characterized by a powder X-ray diffraction pattern having peaks at about 9.1, 16.4, 18.5, 22.8, 23.8 and 24.3±0.2 degrees two-theta.

3. The crystalline form according to claim 2, having additional peaks in the powder X-ray diffraction pattern at about 9.1, 16.4, 18.5, 22.8, 23.8 and 24.3±0.2 degrees two-theta.

Figure 4:
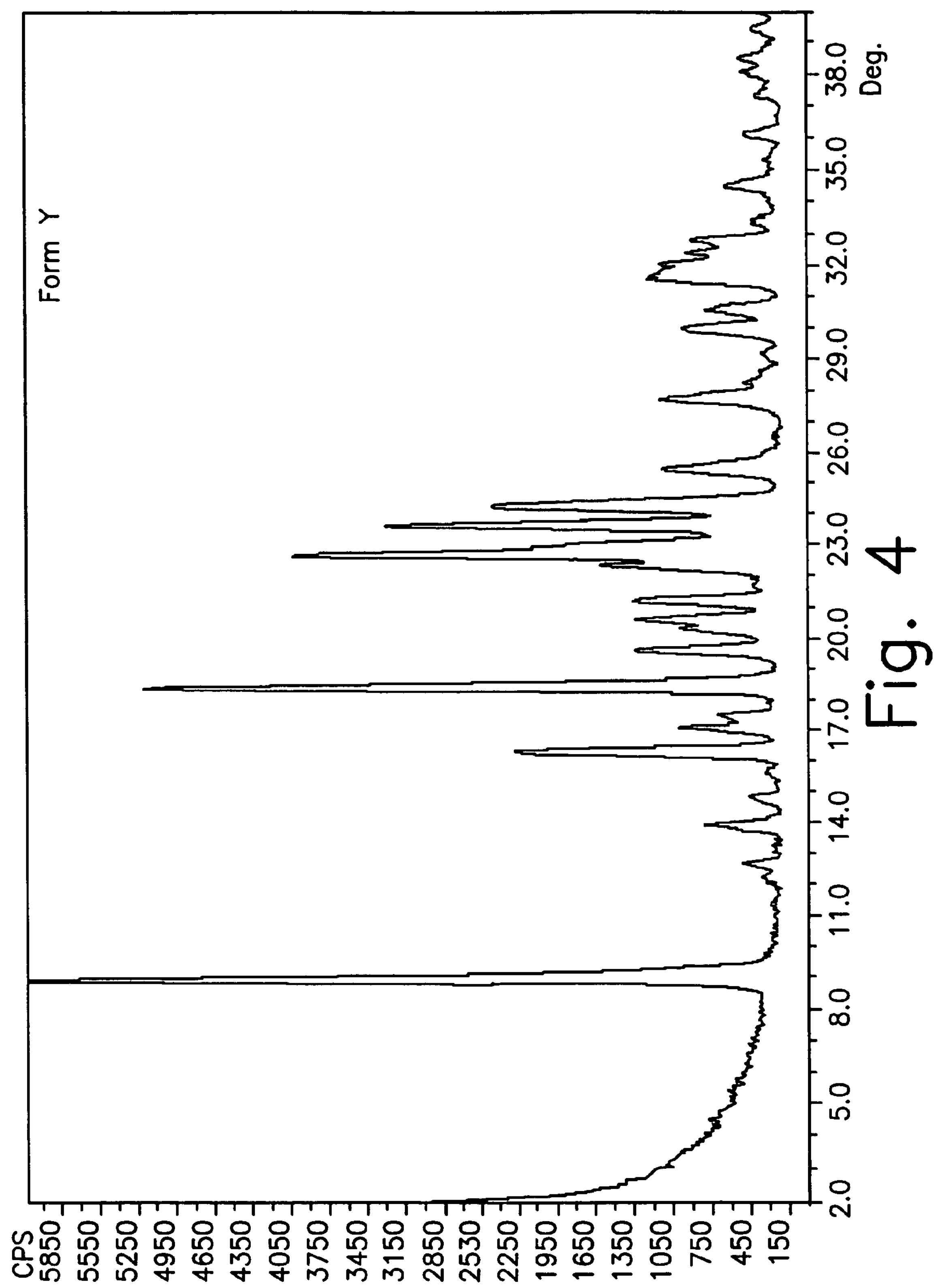
FIG. 4 illustrates the X-ray powder diffraction pattern of olanzapine Form Y.
Figure 5:
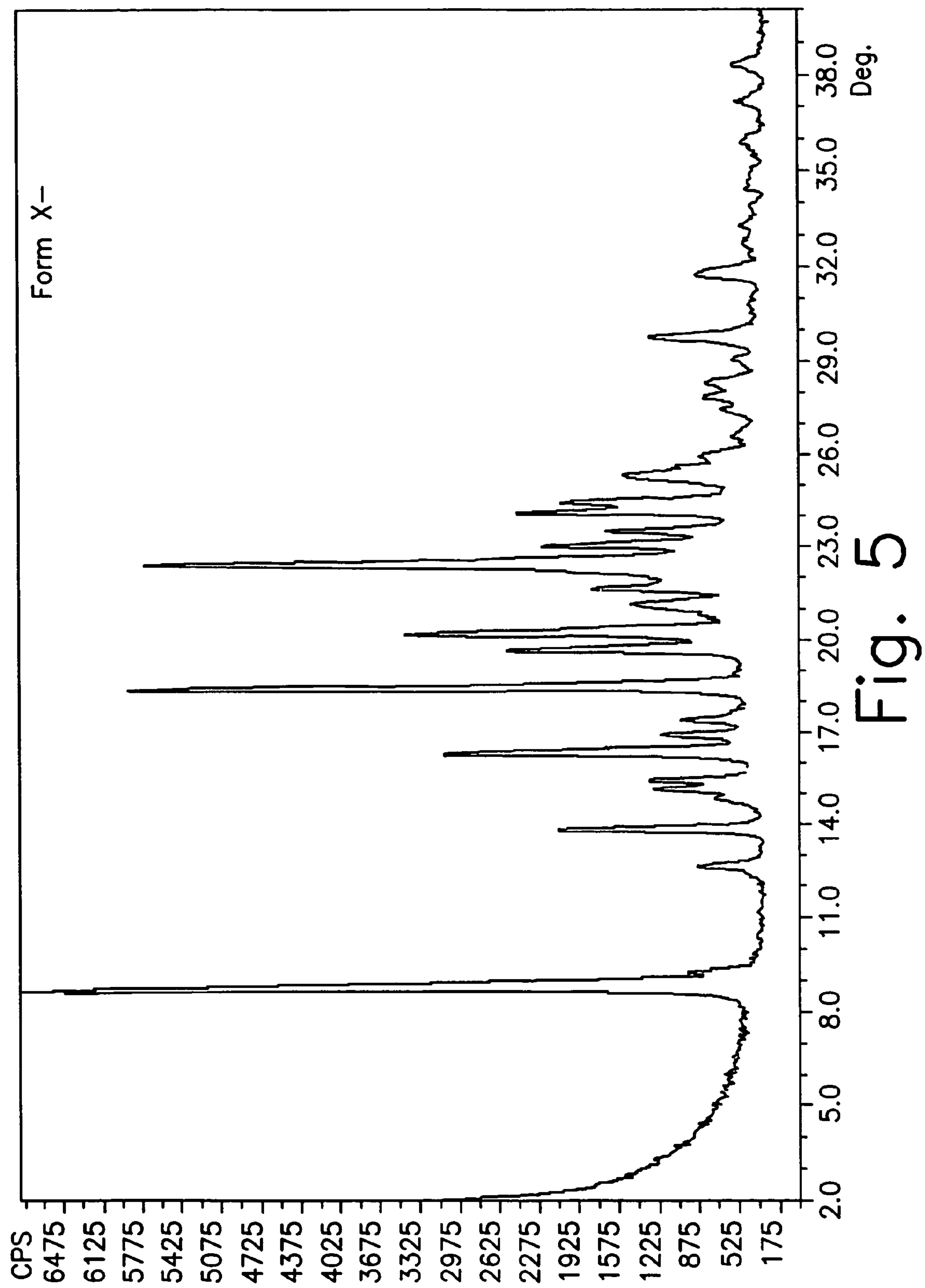
FIG. 5 illustrates the X-ray powder diffraction pattern of olanzapine Form X.
Figure 6:
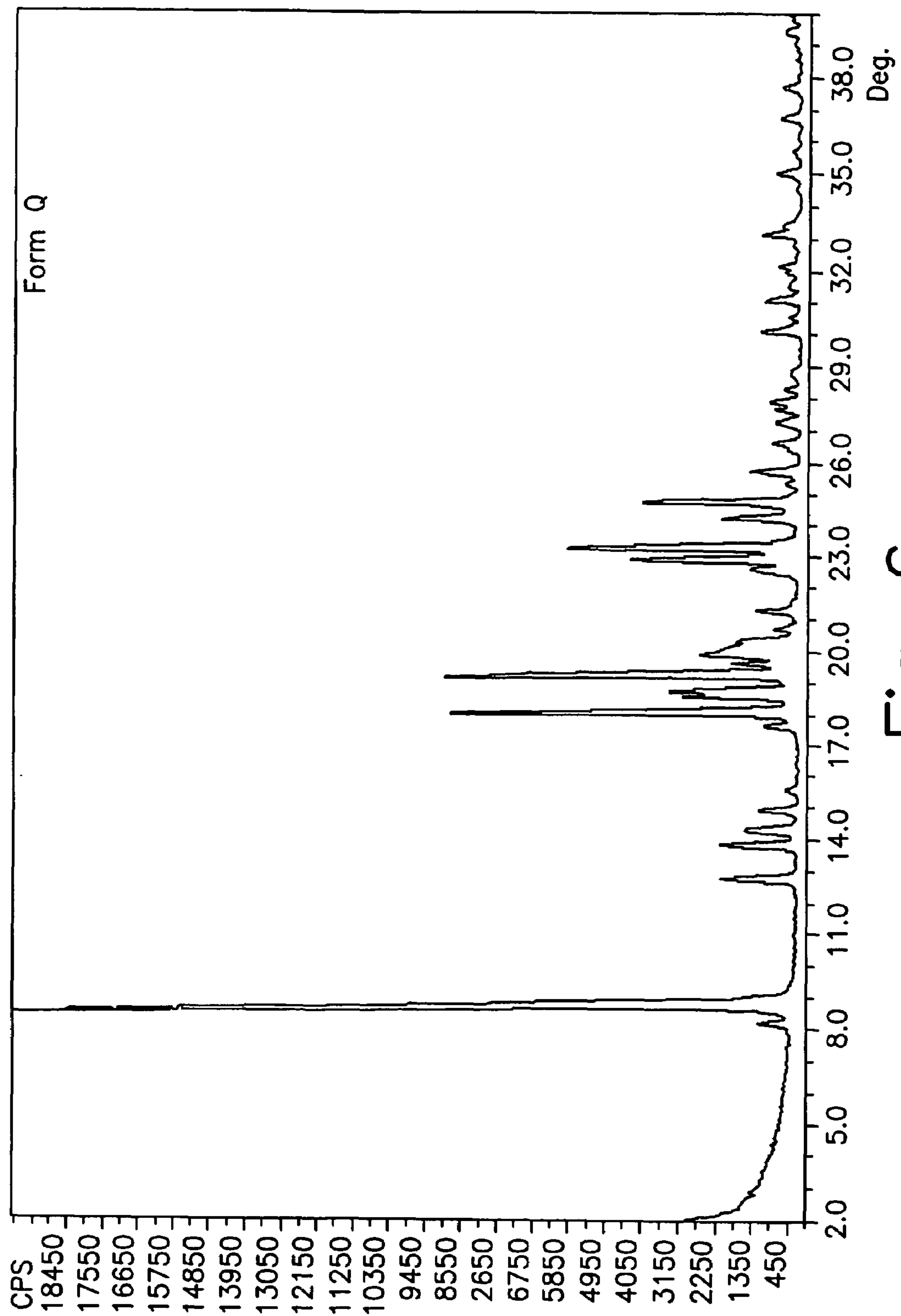
FIG. 6 illustrates the X-ray powder diffraction pattern of olanzapine Form Q.
Figure 7:
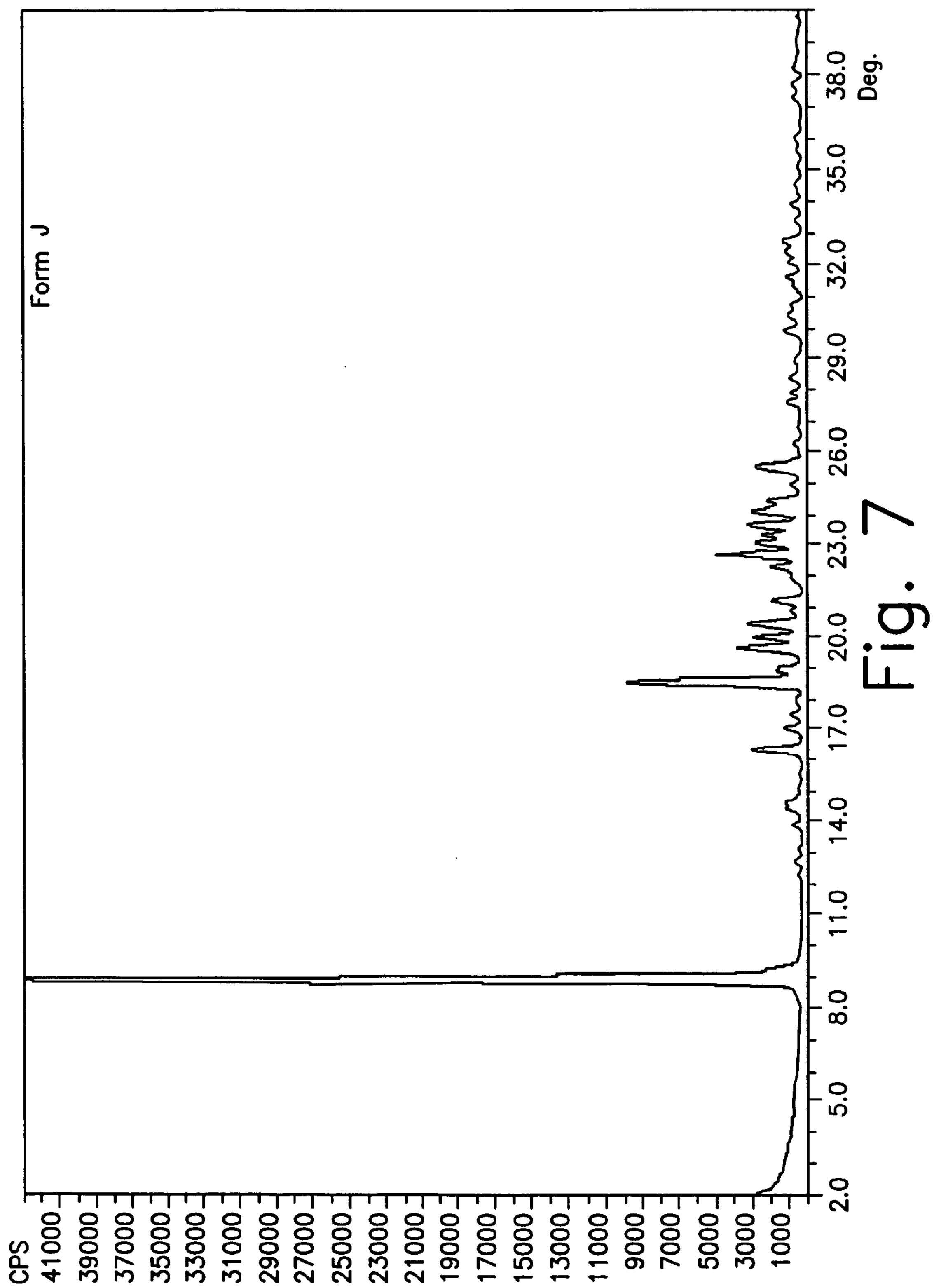
FIG. 7 illustrates the X-ray powder diffraction pattern of olanzapine Form J.

4. The crystalline form of olanzapine according to claim 3, having a powder X-ray diffraction pattern substantially as depicted in FIG. 4.

5. The crystalline form of olanzapine according to claim 2, which is a sesquihydrate.

6. A process for preparing the crystalline form according to claim 2 comprising the steps of:

a) dissolving olanzapine in an aqueous solution of HCl;

b) precipitating the crystalline form by adding base; and c) isolating the crystals.

7. The process of claim 6, wherein olanzapine is dissolved by heating.

8. The process of claim 6, wherein the pH prior to step (c) is about 8.5.

9. The process of claim 6, further comprising cooling the solution prior to step (c).

10. Crystalline olanzapine ¾ hydrate.

11. A crystalline form of olanzapine characterized by a powder X-ray diffraction pattern having peaks at about 8.7, 14.7, 17.1, 17.8, 19.9, 21.0, 21.6, 22.3, 23.9, 25.3 and 26.5±0.2 degrees two-theta.

12. The crystalline form according to claim 11, having additional peaks in the powder X-ray diffraction pattern at about 9.2, 9.4, 10.4, 11.5, 11.9, 12.5 and 29.7±0.2 degrees two-theta.

Figure 8:
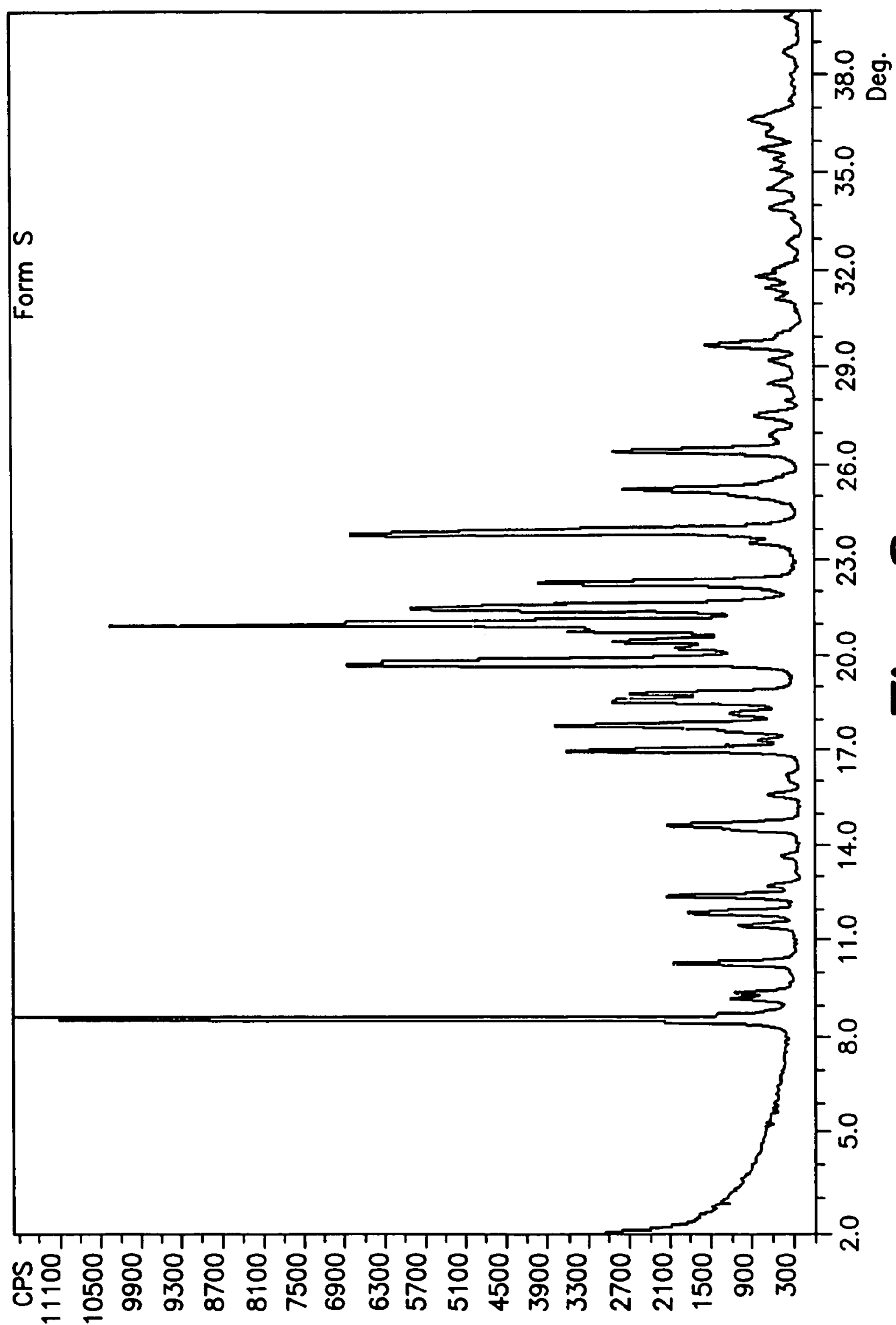
FIG. 8 illustrates the X-ray powder diffraction pattern of olanzapine Form S.
Figure 9:
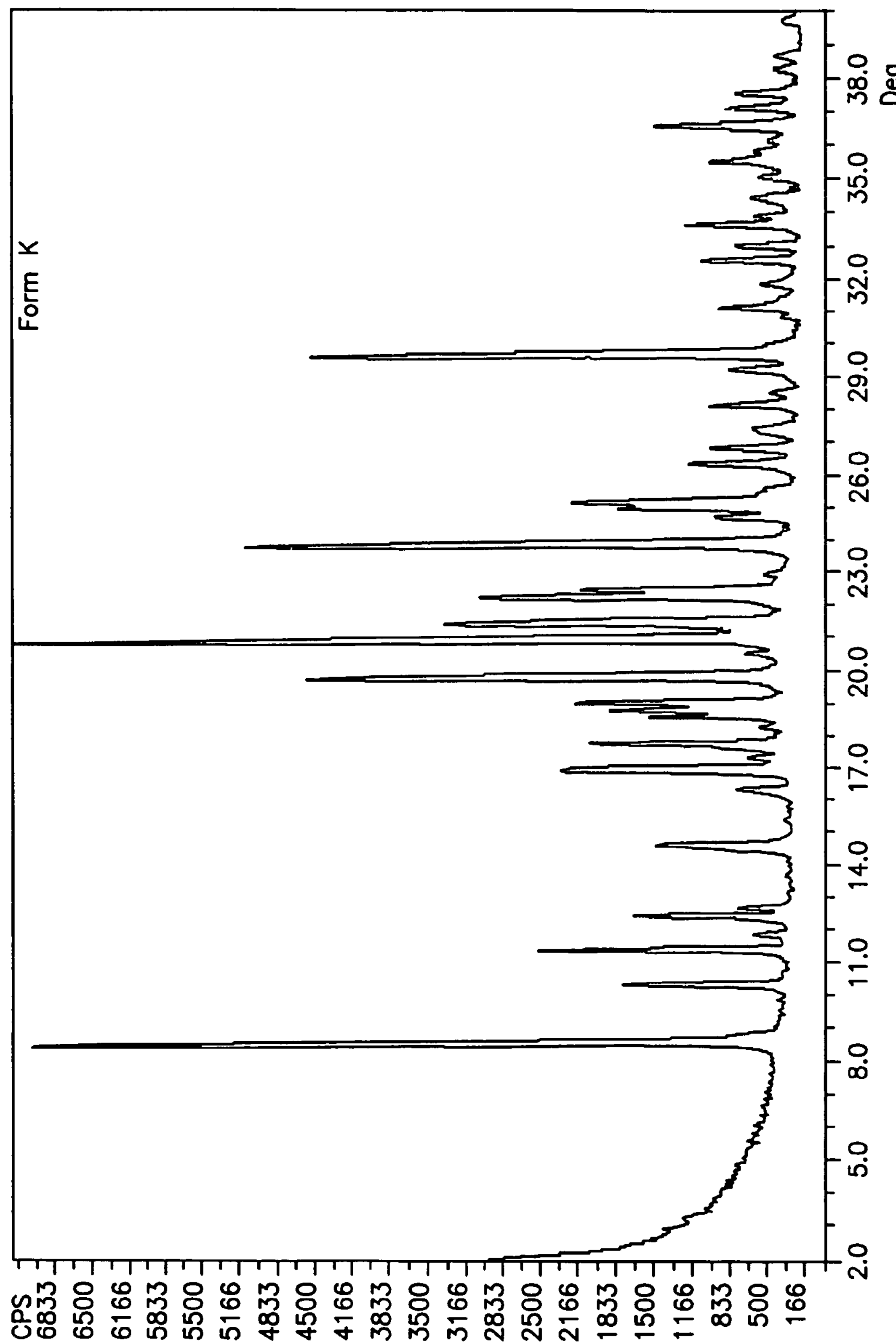
FIG. 9 illustrates the X-ray powder diffraction pattern of olanzapine Form K.

13. The crystalline form of olanzapine according to claim 12, having a powder X-ray diffraction pattern substantially as depicted in FIG. 8.

14. The crystalline form of olanzapine according to claim 11, which is a ¾ hydrate.

15. A process for preparing the crystalline form according to claim 11 comprising the steps of heating Form J at a temperatures of at least about 100° C.

16. The process of claim 15, wherein the heating temperature is about 130° C.

17. A process for preparing the crystalline form according to claim 11 comprising exposing Form II at 100% relative humidity for a period of time ranging between 2 weeks and 2 months.

18. The process of claim 17, wherein the period of time is about 1 month.

* * * * *